United States Patent [19]

Spencer

[11] Patent Number: 4,516,971
[45] Date of Patent: * May 14, 1985

[54] STERILE DOCKING PROCESS, APPARATUS AND SYSTEM

[76] Inventor: Dudley W. C. Spencer, 619 Shipley Rd., Wilmington, Del. 19809

[*] Notice: The portion of the term of this patent subsequent to Jan. 25, 2000 has been disclaimed.

[21] Appl. No.: 395,795

[22] Filed: Jul. 6, 1982

[51] Int. Cl.³ .............................................. A61M 5/00
[52] U.S. Cl. .................................. 604/280; 604/905; 156/304.2; 156/159
[58] Field of Search ................................. 604/905, 29; 156/158–159, 296, 502, 503, 304.2, 304.3, 304.5; 264/156, 159; 425/289, 292; 83/171, 651.1

[56] References Cited
U.S. PATENT DOCUMENTS

3,486,957 12/1969 Fish et al. ........................ 83/171 X
4,000,395 12/1976 Fischer ............................ 83/171 X
4,369,779 1/1983 Spencer ....................... 156/304.2 X Primary Examiner—Stephen C. Pellegrino

[57] ABSTRACT

A process, apparatus and system for making a sterile connection between two thermoplastic resin tubes is disclosed. The tubes are severed by an array of hot wires so as to form molten tube ends. The array is maintained at a temperature such that ambient air immediately within the vicinity of urging is kept sterile. Then, the tubes are aligned with each other and urged together. As the thermoplastic resin cools a sterile weld is formed.

21 Claims, 10 Drawing Figures

STERILE DOCKING PROCESS, APPARATUS AND SYSTEM

BACKGROUND OF THE INVENTION

1. Field of the Invention

This invention relates to a process, apparatus and system for forming a sterile connection (sterile docking) between two tubes.

At the present time there are a number of medical and scientific procedures which require the sterile transfer of fluids from one container to another. The only truly sterile transfer system in current use involves prejoining containers with tubes and then sterilizing the entire assembly. This is inflexible and costly since new containers cannot be added and the number of joined containers needed is often not known at the time of initial filling.

An example of the need for sterile docking is in continuous ambulatory peritoneal dialysis (CAPD). This procedure is replacing dialysis of blood outside the body in membrane diffusion cells where waste products normally removed by kidneys are washed from the blood, which is then returned to the patient. Dialysis outside of the body is a time-consuming procedure and sometimes results in damage to the blood by exposure to materials and conditions external to the body. In CAPD, the patient is required to spend time only for draining spent dialysate and replacing it with a fresh solution.

The CAPD patient has a tube connected to his or her peritoneal cavity via an implanted catheter. A tube from a bag of fresh dialysis solution is connected to the patient's tube. The fresh dialysis solution is drained from the bag into the patient's peritoneal cavity where it remains for about 3-4 hours. During this treatment period, the empty bag is folded and carried by the patient who can continue with his or her normal activities. After this treatment period, the spent dialysate is drained back into the empty bag which is then disconnected from the patient's tube. A bag of fresh dialysis solution is then connected to the patient's tube and the procedure is repeated. Connection to a new bag of dialysis solution exposes the tube ends to airborne bacteria or other contamination even though precautions are taken. No satisfactory way heretofore has existed to insure sterility in spite of the elaborate and costly precautions now employed including the use of masks, gloves, gauze strips and disinfectant solutions. Usually contamination does occur to the extent that a case of peritonitis is contracted perhaps on the average once or more a year and scar tissue from it inhibits dialysis.

Truly sterile connections could minimize the occurrence of peritonitis. Also any other treatment bags, such as for an antibiotic, bacteriostat, or other medication, could be connected as desired.

A similar need for sterile docking exists for blood bags. At present, blood from a donor is drawn into a primary bag which may be joined to one or two satellite bags, all connected and sterilized before use. These satellite bags may be needed for holding blood separated components, such as plasma or platelets; treating agents, such as bases, buffers, stabilizers for cell metabolism, other preservatives, or rejuvenants; or washes to remove a treating agent or other contaminant. Actually, it is not feasible to have preconnected bags for all the treatments which may be desired. Supplemental treatments such as fresh preservative cannot now be added sterilely during bag storage by any commercially acceptable procedure. In addition, to avoid the expense of unused satellite bags, the number of such bags is chosen based on limited, predicted needs. The inability to forecast needs well adds greatly to inventory requirements and complicates scheduling of blood donations.

Currently, very limited use is made of quality control as a time assay of the quantity and quality of components in separated blood factions. The main reason for the current limited use is that heretofore any entry into a sterile blood unit exposed the blood to bacteria, thereby requiring that the blood be used within 24 hours from entry. Hence, although the viability of stored blood components can be extended by supplemental treatments, such as adding a preservative during storage, such treatments are usually not effected.

Moreover, the primary blood bag contains anticoagulant which can be sterilized only by heat (steam); thus all preconnected bags are also sterilized by wet-sterilization techniques, i.e., steam or hot water in an autoclave apparatus. These bags are made of plasticized polyvinyl chloride (PVC), although other materials are known to be useful for constructing bags which are favorable for other reasons, such as greater oxygen permeability. Since many such materials, e.g., oxygen permeable polyethylene, are not steam sterilizable, they are not now used in preconnected systems.

A sterile docking means would permit one to effect whatever processing is desired without compromising sterility, limiting storage life or requiring the preconnection of a multitude of bags, all wet-sterilizable, without knowing which, if any, will be used.

2. References

U.S. Pat. No. 3,013,925 discloses a method of welding two joints of thermoplastic pipe wherein the inside of each end of the joints of pipe to be welded is beveled and the ends of the pipes are heated, for example by pressing the ends of the sections of pipe against a heated plate, after which the ends of the sections are forced together so that flow of softened material is to the outside of the pipe and a weld is effected substantially without formation of a bead on the inside of the welded pipe.

U.S. Pat. No. 3,035,631 discloses a tip for welding plastic parts. The tip has a knife edge at each of two opposing ends. One end of the knife is thick whereas the other is thin. The patent states that as the thin end passes through the joint, it will induce molten plastic surfaces to flow together.

U.S. Pat. No. 3,117,903 discloses a method of joining thermoplastic pipe without forming a troublesome inside ridge at the point of weld, said method involving the immersion of the ends of pipe to be welded in inert high boiling organic liquid heated above the softening temperature of the polymer forming the pipe. Thereby, the ends of the pipe are caused to expand and flare outwardly; then the pipe is withdrawn from the bath and the ends butted together.

U.S. Pat. Nos. 3,769,124 and 3,834,971 disclose a method and apparatus for butt-welding or splicing foam sheet material. The method comprises using a moving hot wire to sever a portion of a leading edge of a new foam stock roll and subsequently to sever a trailing portion of an used roll, discarding the severed portions, aligning horizontally the resulting heat-softened edges of the two rolls, and then bringing the heat-softened edges together to form a butt-weld.

U.S. Pat. No. 3,897,296 discloses a method of welding two plastic surfaces together by juxtapositioning the surfaces, heating the surfaces to a temperature approaching the flash point of the plastic surfaces to liquefy the surfaces, removing a portion of the liquefied surfaces to expose unoxidized surfaces therebeneath and immediately bringing the unoxidized surfaces into abutment with one another. The patent is silent as to cutting a tube as well as forming a sterile dock.

U.S. Pat. No. 3,968,195 discloses a method for making a sterile connection between two rigid tubes the free ends of which have thermoplastic diaphragms which seal off the free ends. When a sterile connection between the free ends of the two tubes is desired, the free ends of each rigid tube are aligned while being spaced slightly apart, and each thermoplastic diaphragm is opened by heating. The free ends of the rigid tubes are then brought into contact and held in position under a slight pressure while the thermoplastic material cools and solidifies, thereby creating a permanent connection. This process requires tubes which have low-melting thermoplastic diaphragms on the ends which can only be used once; i.e., another connection to the same tubing cannot be made.

U.S. Pat. No. 4,209,013 discloses an improvement in a sterile connector system for continuous peritoneal dialysis in which a dialysis solution container having a transfer port is coupled to tubing extending from a patient's peritoneal cavity. The improvement comprises a flexible housing having a first area thereof for attachment to the transfer port and a second spaced area for attachment to the patient's tubing. The attachment areas define openings for enabling the transfer port and patient's tubing to extend within the interior of the flexible housing when they are attached thereto. The flexible housing has means for receiving a sterilizing fluid therein and is operable to enable the transfer port and the patient's tubing to be sterilized within the housing and also connected to each other within the housing.

U.S. Pat. No. 4,223,675 discloses a system for producing sterile, non-autoclavable body fluid containers having autoclaved liquid therein, comprising a dry-sterilized package formed of a material which is unsuitable for being subjected to autoclave conditions, said dry-sterilized package including a sterile communication with the interior of said package; an autoclavable dispenser constructed of an autoclavable substance and containing liquid which was sterilized within the dispenser, said dispenser including a sterile connector having an initially closed sterile aperture in sterile communication with the interior of the dispenser; said package sterile connector and said dispenser sterile connector being in mating engagement with each other.

U.S. Pat. No. 4,242,310 discloses a sterile connection apparatus for enabling the connection of a first tube to a transfer tube of a medical solution container. The apparatus comprises a housing including a base portion and a cover portion adapted for interfitting with each other to provide a substantially closed interior volume. The housing includes means for receiving the first tube, means for receiving the transfer tube from a medical solution container, and means which are located within the housing and operable from outside the housing for enabling manipulation of one of the tubes with respect to the other tube. Means are provided for sterilizing the tube portions within the substantially closed interior volume.

"An Aseptic Fluid Transfer System for Blood and Blood Components," B. A. Myhre et al, Transfusion, Vol. 18, No. 5, pp. 546-552, Sept.-Oct. 1978, describes a process for heat sealing two aseptic fluid transfer system (AFTS) units together. The AFTS units contain a layer of Kapton ® film (an aromatic polyimide resin which is stable at relatively high temperatures). A pair of dies, one of which is flat and one of which has a raised "H" shaped area, are brought together under a pressure of 100 psi ($6.9 \times 10^6$ dynes per square centimeter) with the AFTS units disposed between the dies. The temperature of the dies is raised to 200° C. (392° F.) over a period of 45 seconds. The dies are withdrawn and upon removal of the AFTS units from the dies, the AFTS units are heat sealed together by a seal surrounding an opening between the AFTS units. Blood bags constructed with an AFTS unit attached can thereby be joined. This system is slow and requires specially constructed units that can only be used once.

SUMMARY

The present invention relates to a process, apparatus and system for cutting and joining two sterile, closed end tubes or conduits using a hot severing means while maintaining system sterility. The closed ends of the tubes to be joined are sequentially or simultaneously severed by the severing means. The severing means is maintained at a temperature hot enough to kill bacteria with no chance for viable airborne or surface bacteria to find their way inside either of the tubes or the joint. The tube ends are moved into alignment, the heated severing means slid away, and the ends pushed together, all while maintaining sterility. When the joint cools, the sterile connection or docking is complete. The joint is sound and strong and a number of additional joints can be made in subsequent dockings with the same tube. This invention provides a quick, inexpensive system with no special fittings permitting maximum flexibility in processing, storing and using sterile fluids.

DETAILED DESCRIPTION OF THE INVENTION

Figure 1:
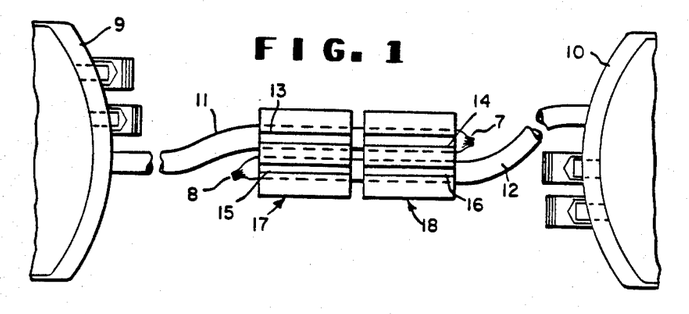
FIG. 1 is a plan view of mounting blocks used to hold two tubes which are to be joined in the starting position.

Referring now to FIG. 1 the sealed end 7 of thermoplastic tube 11 is inserted in slots 13 and 14, machined in blocks 17 and 18. The sealed end 8 of tube 12 is inserted in slots 15 and 16, machined in blocks 17 and 18. Slots 13–14 and 15–16 are aligned to receive straight tubing ends. In FIGS. 1–4, tubes 11 and 12 are connected to blood bags 9 and 10. Alternately, one of said tubes may be connected to a dialysis bag and the other to the patient's peritoneal cavity. Also, the tube which is connected to the patient's peritoneal cavity may be connected at the other end to an empty bag in lieu of having a sealed end.

Figure 2:
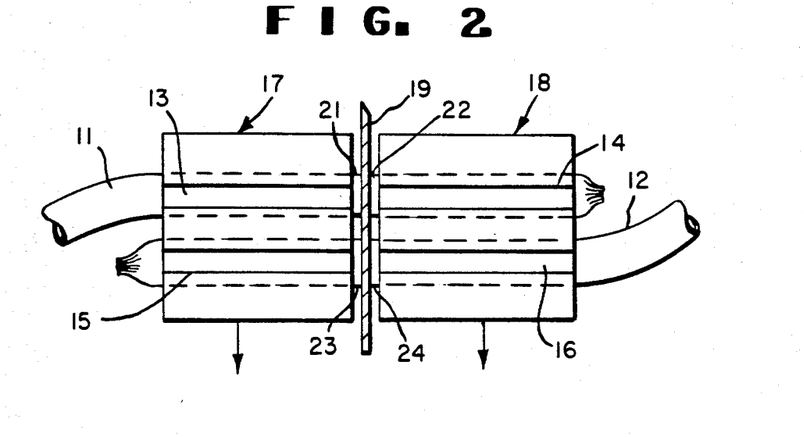
FIG. 2 is a plan view of the two tubes being severed by a hot severing means.

Referring now to FIG. 2, the two blocks 17 and 18 have been slid in the direction shown by the arrows, relative to hot severing means 19, which in the figure is a series of parallel nichrome wires (not shown) fixedly attached to a holder which is open at one side, so that the severing means has melted through tubes 11 and 12 and there are now four molten tube ends 21, 22, 23 and 24.

Figure 3:
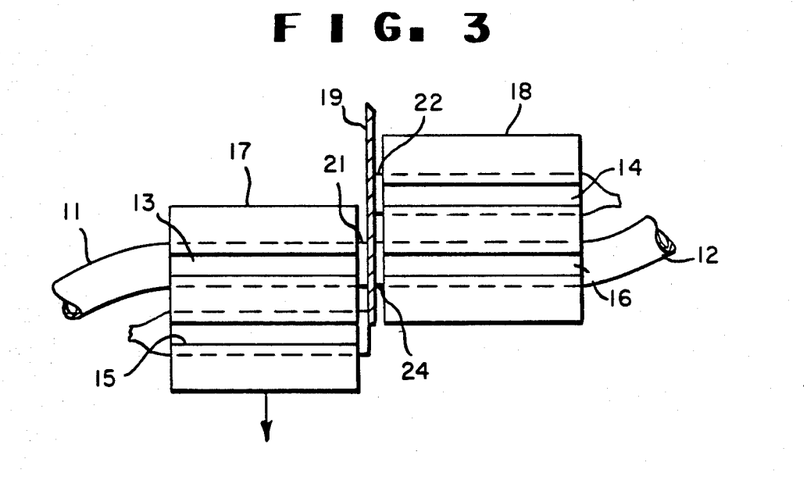
FIG. 3 is a plan view of the two tubes being repositioned and aligned opposite each other.

Referring now to FIG. 3, block 17 has been moved relative to block 18 so that slots 13 and 16 along with tubes 11 and 12 are aligned on opposite sides of the hot severing means.

Figure 4:
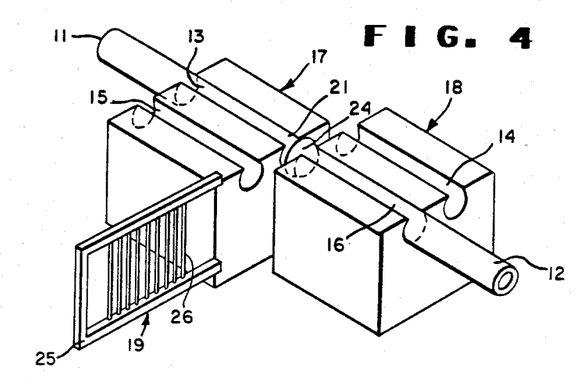
FIG. 4 is a perspective of the mounting blocks, severing means and welded tubes.

Referring now to FIG. 4, blocks 17 and 18, with slots 13 and 16 and tubes 11 and 12 still aligned, and hot severing means 19 comprised of bracket 25 and hot wires 26 have been moved relative to each other and the molten tube ends 21 and 24 have fused and thereby joined tubes 11 and 12 together. The blocks 17 and 18 holding tubes 11 and 12 were urged together by a spring (shown in FIG. 5) during the time when they and severing means 19 were being moved relative to each other, resulting in a slight compression of the joint.

Figure 5:
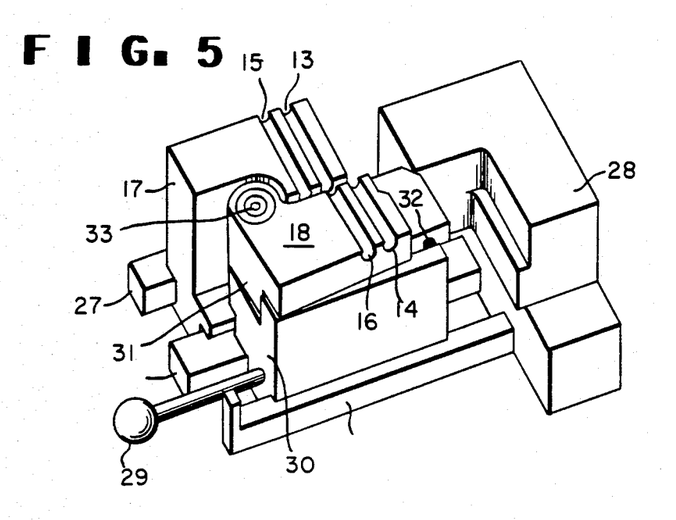
FIG. 5 is a perspective view of the mounting blocks slidably mounted on their guides.

Referring now to FIG. 5, blocks 17 and 18 are shown with slots 13 and 16 aligned and the block in the position after the weld has been made and the welded tubes removed. The blocks are shown slidably mounted in guides 27, 34 and 37. Block 18 is shown as two parts, 30 and 31, which are connected together by bolt 33 so as to allow rotational motion of part 31. Thereby, part 31 can be individually urged by spring 32 toward block 17 as the blocks and tubes (not shown) held thereby are withdrawn from the severing means (not shown for clarity).

Figure 6A:
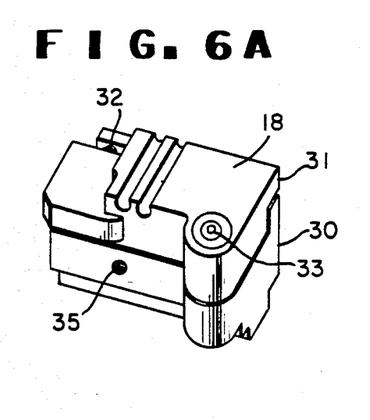
FIGS. 6A and B are perspective views of the mounting blocks.
Figure 6B:
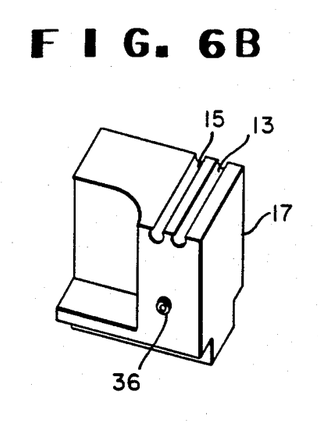
Figure 7:
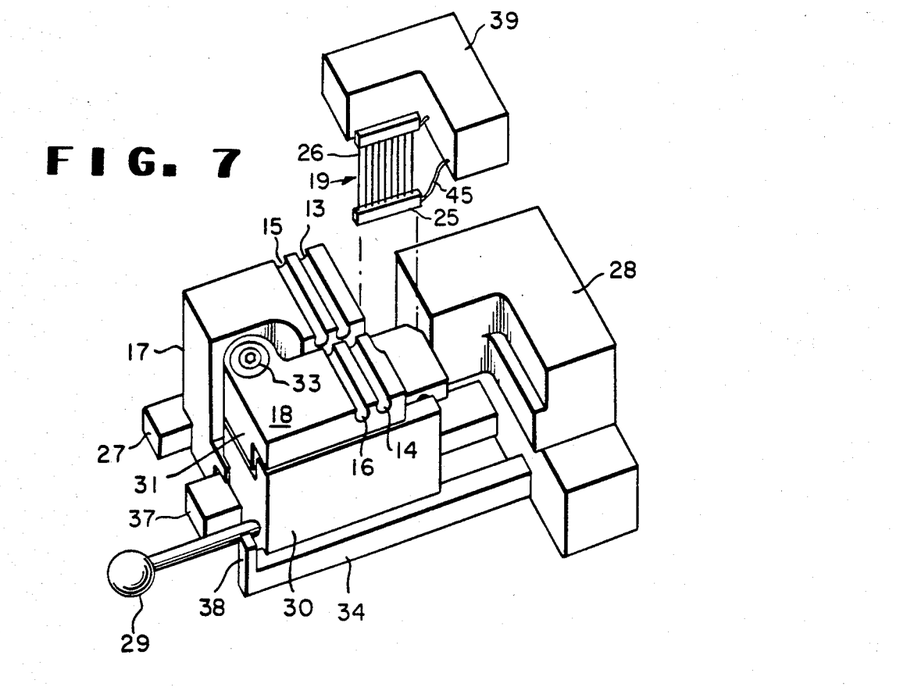
FIG. 7 is a perspective view of the mounting blocks, slidably mounted on their guides and severing means with holding block.
Figure 8:
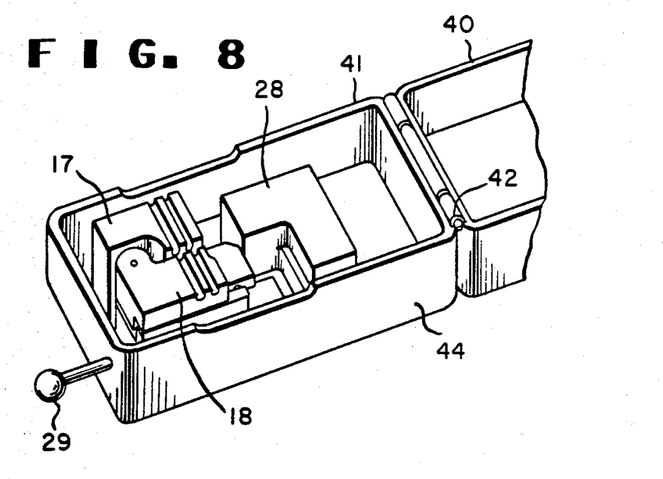
FIG. 8 is a perspective view of the mounting blocks fixedly arranged in a housing.

FIG. 5 also shows operating handle 29 and stop-block 28 against which mounting blocks 17 and 18 are pushed. Operation of this embodiment is best described by using FIGS. 5–8 along with reference to FIGS. 1–3 already described. The operator inserts tube ends in slots 13–14 and 15–16 as shown in FIG. 1. Severing means 19 and block 39 shown in FIG. 7 are lowered so that severing means 19 is positioned between stop-block 28 and mounting blocks 17 and 18 in alignment with the space between said mounting blocks. This positioning is effected by having holding block 39 and severing means 19 fixedly arranged in the upper portion 40 of housing 44 shown in FIG. 8 and the mounting blocks, stop-block 28 and the accompanying slides fixedly arranged in a base portion 41 of housing 44 so that when the housing is closed the severing means is properly situated. The two sections of the housing are attached by hinge 42.

Current for heating the severing means is activated and carried by insulated wires 45 (FIG. 7) to severing means 19. Blocks 17 and 18 shown in FIGS. 6A and B fit together so that the foremost horizontal faces are adjacent. When in the starting position, the mounting blocks are kept in a cooperative relationship by pressure fit of threaded pin 36 on block 17 into cavity 35 in block 18 (FIG. 6). The operator pushes handle 29 which moves blocks 17 and 18 together on slides 27, 34 and 37, thereby moving the tubes across hot severing means 19 as shown in FIG. 2. Block 17 strikes stop-block 28 first thereby causing the two blocks to become sufficiently disengaged so that block 18 moves on to stop against stop-block 28. This further movement by block 18 aligns slots 13 and 16 as shown in FIG. 3. The operator immediately withdraws handle 29 to move block 18 which is connected to the handle 29 and, by friction between the blocks through the pressure exerted by pin 36 on block 18, block 17 also. The blocks and the tube ends to be joined move back away from hot severing means 19. As the corner of block 18 leaves the edge of block 28, spring 32 urges part 31 of block 18 to rotate slightly about bolt 33 toward block 17 so that slight compression is urged on the tube ends being joined as they slide off the hot severing means (see FIG. 5). Stop 38 (FIG. 7) on slide 34 completes the motion of blocks and handle. The operator removes the joined tube after about 5 seconds delay for the joint to cool.

Figure 9:
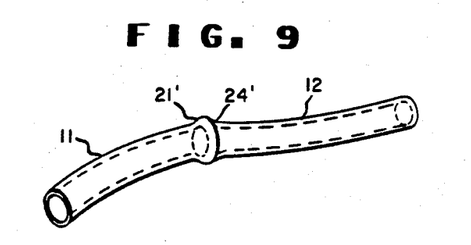
FIG. 9 is a perspective view of the welded tubes.

Referring now to FIG. 9, tubes 11 and 12 are shown joined at now fused molten interfaces 21' and 24' to form a joint which is slightly enlarged due to the pressure exerted by spring 32.

The severing means used in the present invention is an array of parallel hot wires fixed to a holder bracket which is open at one side as shown in FIG. 4. The wires can be made from any suitable resistance-heated metal well known in the art, such as nichrome. A wire gauge of 10 to 20 (American Wire Gauge or Brown and Sharpe standard, 2.59 mm–0.81 mm) is satisfactory, but other sizes can be used. The wires are spaced so that the distance between them is no greater than the radius of the smaller of the two tubes being severed. Preferably, the wires are equally spaced with the distance between them being approximately equal to the diameter of the wires. When the wires are spaced as described herein trailing wires pass across the severed ends of the first tube as the lead wires melt through the second tube. In this manner the severed ends of the first tube and ambient air are maintained in a sterile condition. The wires can be attached to the bracket by using means well known in the art, such as by welding or clamping, and are held in place with heat-resistant, electrically insulating tubes or washers. The bracket 25 can be fixedly attached to block 39 by bolts, magnetic attraction, friction in slots, or other well-known means. The bracket is stiff enough to hold the wires and their insulating washers in place during operation or maintenance.

Currently-used blood and dialysis bags and tubes are made of plasticized polyvinyl chloride for flexibility, strength and steam sterilizing. Generally, for these plasticized polyvinyl chloride tubes, the severing means will be heated to a temperature of from about 500° F. (260° C.) to 750° F. (399° C.) which is also suitable for most other thermoplastic tubing. The severing means preferably is at a temperature high enough (1) to kill rapidly (less than one second) any bacteria or bacterial spores on the outside surface of the tubes and (2) to melt rapidly the thermoplastic resin from which the tubes are formed. The tubes are heat-sealed closed at their ends or connected to a bag. The tubes and whatever bag or bags they are connected to will have been sterilized. Below about 500° F. (260° C.) bacteria and bacterial spores are not rapidly killed by the heat from the severing means. Above about 750° F. (399° C.) most polymers such as plasticized polyvinyl chloride or polyolefins such as polypropylene or polyethylene begin to become too liquid to maintain an even molten end on a tube. About 600° F. (316° C.) is the preferred temperature for use with conventional plasticized polyvinyl chloride blood bag tubing. Another upper limit is the temperature where the resin from which the tube is made begins to degrade in the time it is exposed to the heated severing means (about 2 seconds). For plasticized polyvinyl chloride and polyolefins the upper limit is about 300° F. (149° C.) above the melting point of the thermoplastic resin from which the tube is made.

The tube should be advanced into the severing means at a rate such that the polymer from which the tube is fabricated melts up against the severing means and there should be no mechanical severing of unmolten polymer or significant visible deformation of the tube. Excessive heating times are to be avoided in order to minimize excess melting or degradation of the polymer. For convehtional 165 mil (4.2 mm) outside diameter, 10 mils (0.25 mm) thick wall plasticized polyvinyl chloride blood bag tubing, a time of 0.5 to 1.5 seconds for severing the two tubes has been found to be most satisfactory. The time for repositioning the tubes to align them is not particularly critical but should not be so slow as to cause degraded polymer to be in the welded joint. The speed of withdrawal of the severing means is important to minimize degradation and excess melting and 0.1 to 1 second has been found to be satisfactory. After removal of the hot severing means, cooling of the tubes takes about 5 seconds and the tubes are then removed from the blocks.

The mounting blocks are made of heat conductive metal and serve as heat sinks to assist rapid cooling of the joint. It is necessary that the tubes be urged toward each other as the hot severing means is removed. The space between the blocks and the hot severing means is relatively important. For tubes of about 165 mils (4.2 mm) outside diameter, the spacing between each of the blocks and the surface of the hot severing means should be from about 5 mils (0.13 mm) to 50 mils (1.3 mm), and the preferred spacing between the blocks and the hot severing means being from about 10 mils (0.25 mm) to 20 mils (0.51 mm). With less than about 10 mils (0.25 mm) and especially below about 5 mils (0.13 mm) of tube protruding from a block to the hot severing means there is too much heat loss to the block to maintain an adequate molten polymer seal required to provide a sterile connection. Above about 20 mils (0.51 mm) and especially above about 50 mils (1.3 mm) the exposed tube ends have too much flexibility and the joint may not be sterile. For tubes very much larger than 165 mils (4.2 mm) appropriately larger spacings can be used.

The tubing used should be formed of a thermoplastic resin which melts at least 50° F. below the temperature at which it begins to degrade in the time exposed to heat in the process of the present invention. The tubes to be connected are preferably of the same diameter but can have different diameters so long as a complete seal having about 50% of the original tube strength can be made. The tubes to be joined can be made of the same material or can be made of compatible resins. "Compatible resins" as used herein means that the melting points of the two materials are close enough so that at the operating temperature both form thick, viscous melts which will flow together to form a single melt phase without polymer degradation or formation of thermal or other chemical reaction products which would weaken or otherwise interfere with formation of the single melt phase and its subsequent cooling and solidification to a strong joint. For example, polyethylene is compatible with polyethylene copolymers and polypropylene.

In order to obtain a secure dock, tubes to be joined must not contain more liquid than a thin film on the walls at or near the locations where they are to be cut and joined. Generally, the length of tubing which is empty of liquid need not be more than about 0.5 to 1 inch (13–25 mm).

The apparatus of the invention can form part of a sterile connection system for continuous ambulatory peritoneal dialysis in which a dialysis solution container with a transfer port that includes a segment of tubing is coupled to a tube extending from an implanted catheter opening into a patient's peritoneal cavity. In this embodiment of the invention the patient's tube and/or the transfer tube can have an entry port with a protective cover or a sealed distal end but preferably both have a sealed distal end. This system minimizes the possibility of peritonitis and permits any other treatment bag, such as a bag of antibiotic, bacteriostat, or other medication to be connected as desired. Moreover, this embodiment offers the additional advantage of eliminating the need for the patient to carry the empty dialysis solution bag because the bag can be sterilely disconnected and the patient's tube can be joined to a sterile sealed-end tube. It also eliminates the need for the present laborious procedure used to achieve sterility.

In another embodiment, the apparatus of the invention forms part of a sterile connection system for connecting two blood bags. One of the bags can be a donor bag and the other a transfer bag. The donor bag will have a blood collection tube and optionally can have a transfer port with a transfer tube. The transfer bag has a transfer tube (connection tube). The two bags can be sterilely connected by joining the connection tube of the transfer bag to the transfer port of the donor bag. The transfer port of the donor bag can be a conventional entry port, e.g., having a protective covering and a septum inside the port. The bags can also be connected by joining the blood collection tube of the donor bag to the connection tube of the transfer bag. In another embodiment, the blood collection tube and the connection tube of the transfer bag both have a sealed distal end.

In the preferred embodiment for both the blood bag system and the CAPD system, the donor bag and dialysis bag have, specifically for sterile connection, an additional tube (pigtail) which is connector-free and has a sealed distal end. The term "connector-free" as used herein means the tube does not bear any of the conventional fittings, such as a plastic fitting with a diaphragm, a low-melting thermoplastic insert, an insert fusable by radiant energy, or the like. The tube has a sealed distal end which is prepared solely by sealing the tube end together by use of heat, solvent or the like. This modified bag is further described in copending U.S. application Ser. No. 267,291, the relevant disclosure of which is incorporated herein by reference. The tube is equipped with means, such as a clamp, to prevent undesired flow of liquid into said tube.

In the present system for the sterile connection of blood bags, the need to pre-assemble bags into a system is eliminated. It is to be understood that the expression "blood bag" as used herein refers collectively to either the donor (primary) bag or the satellite bag. With the present invention satellite bags can be sterilely connected to a donor bag as the need arises. The donor bag can be made from a wet-sterilizable material, such as polyvinyl chloride whereas the satellite bags do not have to be wet-sterilizable but can be made of material which can be sterilized only by dry-sterilization means, such as irradiation or ethylene oxide treatment. For example, the satellite bag can be constructed from $O_2$ permeable polyethylene which would increase platelet viability. Alternatively, the satellite bag can be made from a polyethylene copolymer, a polyethylene laminate, polypropylene, or any other material which is compatible with the material from which the donor bag is constructed. The satellite bag can be made from material which is incompatible with the material from which the donor bag is constructed so long as the tubes to be connected are made of compatible materials. For instance, the donor bag and its tubing can be made from polyvinyl chloride whereas the satellite bag can be made from polyethylene but its tubing made from polyvinyl chloride and solvent welded to the satellite bag. Techniques for solvent welding are well known in the art. Supplemental treatments can be sterilely added and washing to remove treating agents can be sterilely effected. Some practitioners believe hepatitis risks can be reduced by washing red cells without previous freezing.

The sterile docking apparatus of the invention can also be used to provide a system for producing sterile, non-autoclavable body fluid containers having wet-sterilized (autoclaved) liquid therein. The system is similar to that described in U.S. Pat. No. 4,223,675; however, the present apparatus eliminates the need to have special connectors attached to the tubing.

With the present invention a dry-sterilized package can be formed from a synthetic resin material which is unsuitable for being subjected to wet-sterilization conditions but is particularly suitable for prolonged storage of body fluids. The autoclavable liquid is placed in an autoclavable dispenser equipped with an access tube which can then be heat-sealed closed. The dispenser package and liquid are then wet-sterilized in an autoclave. The dispenser package is next sterilely connected to a dry-sterilized container by using the apparatus and process of the invention. The dry-sterilized container can be equipped with a connector-free tube having a sealed distal end, said tube being specifically for sterile connection. After the sterile connection is made the autoclaved liquid is transferred to the dry-sterilized container which is non-autoclavable. If desired, the two containers can be separated by heat sealing the connecting tube while moving the containers apart so that each container is left with a connector-free tube having a sealed distal end. Other packages can be connected to either container by subsequent sterile docking operations. The autoclavable liquid can be an anticoagulant and the autoclavable dispenser package can be constructed from polyvinyl chloride. The non-autoclavable container can be a blood bag constructed from materials such as those previously described herein.

The process of the invention for joining two thermoplastic tubes together transversely of the axis of each tube comprises urging hot severing means through both said tubes at a rate such that the thermoplastic resin from which said tubes are formed and which is in contact with said severing means becomes molten thereby forming molten ends, maintaining the severing means at a temperature such that ambient air immediately within the vicinity of urging is kept sterile, joining the respective molten ends of said tubes together to form a joint between said tubes and cooling the resulting joint. As used herein, transverse means crosswise the axis of each tube but not necessarily at right angle with each tube. The process of the invention can be carried out using the herein-described specific embodiment of the apparatus of the invention but is not limited thereto. The conditions of operations are those previously set forth herein.

I claim:

1. A process of joining first and second thermoplastic tubes together transversely of the axis of each tube comprising urging an array of hot parallel wires through both said tubes at a rate such that the thermoplastic resin from which said tubes are formed and which is in contact with said array becomes molten, thereby forming molten ends, maintaining the array of parallel wires at a temperature such that ambient air immediately within the vicinity of urging is kept sterile, moving the respective molten ends of said tubes together to form a joint between said tubes.

2. A process of forming a sterile connection between a first tube and a second tube, both formed of a thermoplastic resin, comprising mounting said tubes in a pair of mounting means which hold said tubes in a closely adjacent substantially parallel position, urging an array of hot parallel wires through both said tubes at a rate such that the thermoplastic resin from which said tubes are formed and which is in contact with said array becomes molten, thereby forming molten ends, maintaining said array of parallel wires at a temperature such that ambient air immediately within the area of urging is kept sterile, aligning said tubes with each other, urging said tubes together while separating them and said array, and cooling the thusly joined tube ends whereby a sterile connection is formed between said tubes.

3. A process according to claim 2 wherein the array of hot parallel wires is maintained at a temperature above about 260° C.

4. A process according to claim 3 wherein the array of hot parallel wires is maintained at a temperature below the temperature where the thermoplastic resin from which the tubes are made begins to degrade in the time used.

5. A process according to claim 4 wherein the wires in the array of hot parallel wires are equally spaced apart with the distance between said wires being about equal to or less than the diameter of the wires.

6. An apparatus for forming a sterile connection comprising
an array of parallel wires; means adapted to heat said array of parallel wires;
a pair of mounting blocks adapted to receive and hold two tubes to be joined, said array of parallel wires being movably located between said blocks;
means adapted to traverse said array of parallel wires where the mounting blocks are adapted to receive tubes and to separate said array and said blocks;
means for aligning said blocks to a position where two different tube ends to be joined are aligned with and facing each other;
means for urging said blocks together while separating said blocks and said array of parallel wires.

7. An apparatus according to claim 6 wherein wires in the array of parallel wires are equally spaced apart with the distance between said wires being about equal to or less than the diameter of the wires.

8. An apparatus according to claim 7 wherein the blocks are spaced from about 0.13 to 1.3 mm from said array of parallel wires when said array is positioned between said blocks.

9. A sterile connection system for continuous ambulatory peritoneal dialysis in which a dialysis solution container with a transfer port that includes a segment of tubing is coupled to a tube extending from a patient's peritoneal cavity, wherein the improvement comprises a pair of mounting blocks adapted to receive and hold the transfer port tube and the patient's tube; movable array of parallel wires located between said blocks; means adapted to heat said array of parallel wires; means adapted to traverse said array of parallel wires where the mounting blocks are adapted to receive said tubes and to separate said array and said blocks; means for aligning said blocks to a position where two different tube ends to be joined are aligned with and facing each other; and means for urging said blocks together while separating said blocks and said array of parallel wires.

10. A sterile connection system according to claim 9 wherein the patient's tube is connector-free and has a sealed distal end.

11. A sterile connection system according to claim 10 wherein the transfer port tube is connector-free has a sealed distal end, and is the same diameter as that of the patient's tube.

12. A sterile connection system for joining two blood bags, each bag having a tube which can be used for connection and sterile connection being made by joining said tubes, wherein the improvement comprises a pair of mounting blocks adapted to receive and hold the tubes to be joined; movable array of parallel wires located between said blocks; means adapted to heat said array of parallel wires; means adapted to traverse said array of parallel wires where the mounting blocks are adapted to receive said tubes and to separate said array of parallel wires and said blocks; means for aligning said blocks to a position where two different tube ends to be joined are aligned with and facing each other; and means for urging said blocks together while separating said blocks and said array.

13. A sterile connection system according to claim 12 wherein one of the bags is a donor bag and its blood collection tube is one of the tubes to be joined.

14. A sterile connection system according to claim 13 wherein the two tubes to be joined are of the same diameter.

15. A sterile connection system according to claim 14 wherein the blood collection tube has a sealed distal end.

16. A sterile connection system according to claim 15 wherein the second bag is a transfer bag having a transfer port with a transfer tube and the transfer tube is the other tube to be joined.

17. A sterile connection system according to claim 16 wherein the transfer tube has a sealed distal end.

18. A sterile connection system according to claim 12 wherein one of the bags is a donor bag having, in addition to its blood collection tube, a connector-free tube to be used specifically for sterile connection, said tube having a sealed distal end.

19. A sterile connection system according to claim 18 wherein the donor bag is steam sterilizable and the other bag is a transfer bag made from material which is dry sterilizable only.

20. A sterile connection system according to claim 19 wherein the transfer bag has a connector-free tube having a sealed distal end.

21. A sterile connection system according to claim 20 wherein the two tubes to be connected are of the same diameter.

* * * * *